United States Patent [19]

Barth

[11] 4,364,957
[45] * Dec. 21, 1982

[54] BIS-ESTERS OF ALKANEDIOLS AS ANTIBACTERIAL AGENTS

[75] Inventor: Wayne E. Barth, East Lyme, Conn.

[73] Assignee: Pfizer Inc., New York, N.Y.

[*] Notice: The portion of the term of this patent subsequent to Mar. 17, 1998, has been disclaimed.

[21] Appl. No.: 236,407

[22] Filed: Feb. 20, 1981

Related U.S. Application Data

[63] Continuation-in-part of Ser. No. 79,127, Sep. 26, 1979, Pat. No. 4,256,733.

[51] Int. Cl.$^3$ .................. C07D 499/44; A61K 31/43
[52] U.S. Cl. ............................ 424/271; 260/245.2 R; 260/239.1; 424/270; 424/114
[58] Field of Search .................. 260/245.2 R, 239.1; 424/271, 270, 114

[56] References Cited

U.S. PATENT DOCUMENTS

| | | | |
|---|---|---|---|
| 4,234,579 | 11/1980 | Barth | 424/246 |
| 4,244,951 | 1/1981 | Bigham | 424/250 |
| 4,256,733 | 4/1981 | Barth | 424/114 |

FOREIGN PATENT DOCUMENTS 881675  8/1980  Belgium .

*Primary Examiner*—Nicholas S. Rizzo
*Attorney, Agent, or Firm*—Charles J. Knuth; Albert E. Frost; J. Trevor Lumb

[57] ABSTRACT

6-Acylaminopenicillanoyloxymethyl esters and 1-(6-acylaminopenicillanoyloxy)ethyl esters of 2-beta-acetoxymethyl-2-alpha-methyl-(5R)penam-3-alpha-carboxylic acid 1,1-dioxide are useful as antibacterial agents. The 6-aminopenicillanoyloxymethyl ester, the 1-(6-aminopenicillanoyloxy)ethyl ester and certain other mono-substituted methyl and ethyl esters of 2-beta-acetoxymethyl-2-alpha-methyl-(5R)penam-3-alpha-carboxylic acid 1,1-dioxide are useful intermediates to the aforesaid antibacterial agents.

9 Claims, No Drawings

BIS-ESTERS OF ALKANEDIOLS AS ANTIBACTERIAL AGENTS

CROSS-REFERENCE TO RELATED APPLICATIONS

This application is a continuation-in-part of application Ser. No. 079,127, filed Sept. 26, 1979, and now U.S. Pat. No. 4,256,733.

BACKGROUND OF THE INVENTION

This invention relates to new chemical compounds. More particularly it relates to new chemical compounds which are of value as antibacterial agents. These new antibacterial agents are bis-esters of methanediol and 1,1-ethanediol, in which one hydroxy group of the diol has been esterified with the carboxy group of a 6-acylaminopenicillanic acid, and the other hydroxy group of the given diol has been esterified with the carboxy group of 2-beta-acetoxymethyl-2-alpha-methyl-(5R)penam-3-alpha-carboxylic acid 1,1-dioxide.

In addition, this invention relates to the 6-aminopenicillanoyloxymethyl and the 1-(6-aminopenicillanoyloxy)ethyl esters of 2-acetoxymethyl-2-beta-methyl-(5R)penam-3-alpha-carboxylic acid 1,1-dioxide. These latter compounds are useful as intermediates to the antibacterial agents of this invention.

Still further, this invention relates to certain halomethyl, alkylsulfonyloxymethyl, arylsulfonyloxymethyl, 1-haloethyl, 1-(alkylsulfonyloxy)ethyl and 1-(arylsulfonyloxy)ethyl esters of 2-beta-acetoxymethyl-2-alpha-methyl-(5R)penam-3-alpha-carboxylic acid 1,1-dioxide. Said latter compounds are also useful as intermediates to the antibacterial agents of this invention.

U.S. Pat. No. 4,244,951 and Belgium Pat. No. 881,675 disclose bis-esters of 1,1-alkanediols in which one of the hydroxy groups of the 1,1-alkanediol has been esterified with the carboxy group of a beta-lactamase inhibitor, e.g. penicillanic acid 1,1-dioxide. Said United States and Belgian patents also disclose a variety of intermediates to said bis-esters of 1,1-alkanediols.

The antibacterial agents of the present invention are efficiently absorbed from the gastrointestinal tract of mammals, and after absorption they are transformed into a 6-acylaminopenicillanic acid and 2-beta-acetoxymethyl-2-alpha-methyl-(5R)penam-3-alpha-carboxylic acid 1,1-dioxide.

SUMMARY OF THE INVENTION

This invention provides new antibacterial agents of the formula

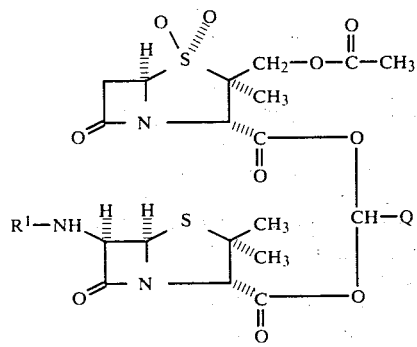

(I)

and the pharmaceutically-acceptable salts thereof, wherein $R^1$ is an acyl group of an organic carboxylic acid, and Q is selected from the group consisting of hydrogen and methyl. However, preferred compounds of the formula I are those in which $R^1$ is an acyl group known from a natural, biosynthetic or semisynthetic penicillin compound. Especially preferred compounds of the formula I are those in which $R^1$ is selected from the group consisting of 2-phenylacetyl, 2-phenoxyacetyl, 2-amino-2-phenylacetyl, 2-amino-2-[4-hydroxyphenyl]acetyl and 2-carboxy-2-phenylacetyl.

Preferred individual compounds of the invention are:

6'-(2-amino-2-phenylacetamido)penicillanoyloxymethyl 2-beta-acetoxymethyl-2-alpha-methyl-(5R)penam-3-alpha-carboxylate 1,1-dioxide and 6'-(2-amino-2-[4-hydroxyphenyl]acetamido)penicillanoyloxymethyl 2-beta-acetoxymethyl-2-alpha-methyl-(5R)penam-3-alpha-carboxylate 1,1-dioxide.

This invention also provides compounds of the formula:

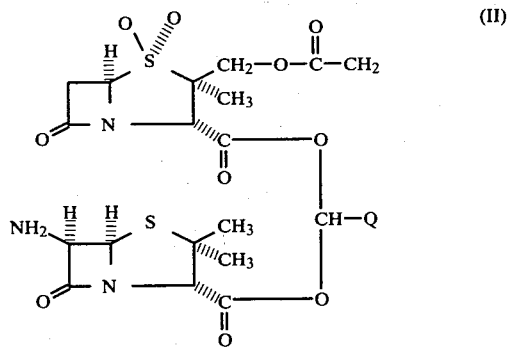

(II)

and

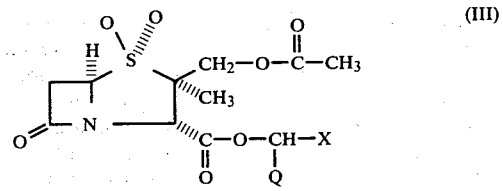

(III)

and the salts thereof, wherein X is a good leaving group, and Q is selected from the group consisting of hydrogen and methyl. Examples of X are chloro, bromo, iodo, alkylsulfonyloxy having from one to four carbon atoms, phenylsulfonyloxy and tolylsulfonyloxy. The compounds of formulae II and III are useful as intermediates to the antibacterial agents of the invention.

DETAILED DESCRIPTION OF THE INVENTION

In this specification, the term "penicillanic acid" refers to the structural formula

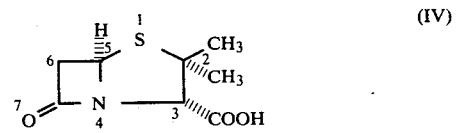

(IV)

and the term "(5R)penam" refers to the structural formula

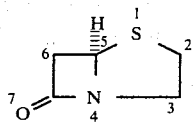

In formulae IV and V, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration. Accordingly, the antibacterial agents of formula I are named as derivatives of penicillanoyloxymethyl 2-beta-acetoxymethyl-2-alpha-methyl-(5R)penam-3-alpha-carboxylate (VA; Q is hydrogen) and 1-(penicillanoyloxy)ethyl 2-beta-acetoxymethyl-2-alpha-methyl-(5R)penam-3-alpha-carboxylate (VA; Q is methyl). Primed and unprimed locants are used to distinguish between the two ring systems, viz:

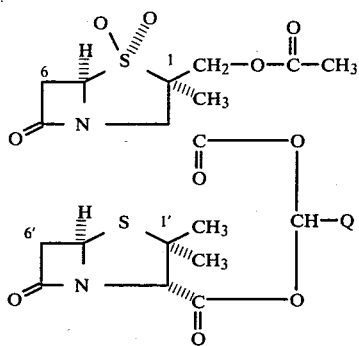

Additionally, throughout this specification, whenever reference is made to a compound which has a 2-amino-2-(substituted)acetamido or 2-azido-2-(substituted)acetamido group at the 6-position of a penicillanic acid derivative, it is to be understood that this refers to a compound in which said 2-amino-2-(substituted)acetamido or 2-azido-2-(substituted)-acetamido has the D-configuration.

In one method according to the invention a compound of formula I can be prepared by reacting a carboxylate salt of the formula

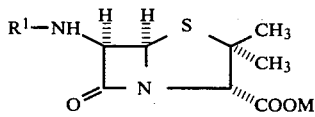

with a compound of the formula

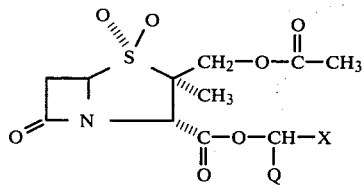

wherein $R^1$, Q and X are as previously defined, and M is a carboxylate salt forming cation. A variety of cations can be used to form the carboxylate salt in the compound of formula VI, but salts which are commonly used include: alkali metal salts, such as sodium and potassium salts; alkaline earth metal salts, such as calcium and barium salts; tertiary amine salts, such as trimethylamine, triethylamine, tributylamine, diisopropylethylamine, N-methylmorpholine, N-methylpiperidine, N-methylpyrrolidine and N,N'-dimethylpiperazine salts; and tetraalkylammonium salts, such as tetramethylammonium and tetrabutylammonium salts.

The reaction between a compound of formula VI and a compound of formula III is usually carried out by contacting the reagents in a polar, organic solvent, at a temperature in the range from about 0° to about 80° C., and preferably from 25° to 50° C. The compounds of formulae VI and III are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. Typical solvents which can be used include N,N-dimethylformamide, N,N-dimethylacetamide, N-methylpyrrolidone, dimethylsulfoxide and hexamethylphosphoramide. The reaction time varies according to a number of factors, but at about 25° C. reaction times from a few minutes to about 24 hours, are used. When X is chloro or bromo, it is sometimes advantageous to add up to about one molar equivalent of an alkali metal iodide, which has the effect of speeding up the reaction.

The compound of formula I is isolated in conventional fashion. When a water-miscible solvent is used, it is usually sufficient simply to dilute the reaction medium with an excess of water. The product is then extracted into a water immiscible solvent, such as ethyl acetate, and then the product is recovered by solvent evaporation. When a water immiscible solvent is used, it is usually sufficient to wash the solvent with water, and then recover the product by solvent evaporation. The compound of formula I can be purified by well-known methods, such as recrystallization or chromatography, but due regard must be given to the lability of the beta-lactam ring system.

When the group $R^1$ in a compound of formula VI contains a basic group, such as a primary amino group, this group can interfere during the reaction with the ester III. In this case it is usually advantageous to protect the amino group in $R^1$ before contacting the compound of formula VI with the compound of formula III. A variety of conventional amino protecting groups can be used for this purpose. The only requirements for such a group are that: (a) it can be affixed to the compound of formula VI under conditions which do not adversely affect the compound of formula VI; (b) it is stable under the conditions under which the compound of formula VI reacts with the compound of formula III; and (c) it can be removed after the reaction with the compound of formula III is complete, using conditions which do not adversely affect the compound of formula I. Typical amino protecting groups which can be used are benzyloxycarbonyl, substituted benzyloxycarbonyl, 2-nitrophenylsulfenyl and 2,2,2-trichloroethoxycarbonyl. Benzyloxy-carbonyl and 4-nitrobenzyloxycarbonyl are particularly convenient groups.

Alternatively, when it is desired to prepare a compound of formula I in which $R^1$ contains a basic, primary amino group, it is possible to carry out the reaction between the compounds of formula VI and III with a pro-amino group at the appropriate location in the group $R^1$ in the compound of formula VI. After the reaction between the compounds of formulae VI and III has been carried out, the pro-amino group is converted into an amino group. A pro-amino group is a group which is not adversely affected during the reaction between the compounds of formulae VI and III, and which can be converted into an amino group under conditions which do not adversely affect the rest of the molecule in said compound of formula I. A useful pro-amino group is an azido group. It can be converted into an amino group by catalytic hydrogenation, e.g. using 10% palladium-on-carbon.

When the group $R^1$ in a compound of formula VI contains a carboxy group, it is usual to protect this carboxy group before the reaction with the compound of formula III, particularly when the carboxy group is subject to ready decarboxylation. In this case it is advantageous to start with a compound of formula VI in which the carboxy group in $R^1$ is in the form of a readily hydrolyzable ester, e.g. a phenyl or substituted phenyl ester. After the coupling with the compound of formula III is complete, the free carboxy group in $R^1$ is liberated by mild, alkaline hydrolysis, e.g. using the technique disclosed in U.S. Pat. No. 3,679,801. This methodology is especially useful when $R^1$ is a group such as 2-carboxy-2-phenylacetyl.

A variation of the foregoing method of preparing a compound of formula I involves reaction of a compound of the formula

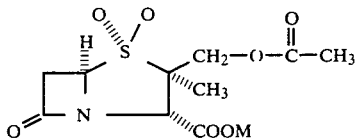

with a compound of the formula

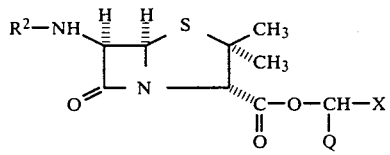

wherein Q, M and X are as defined previously, and $R^2$ is the group $R^1$, but with any free amino groups and/or carboxy groups protected, followed if necessary by removal of any amino or carboxy protecting group. In the compounds of formula VIII, the free amino groups and the carboxy groups are protected with exactly the same protecting groups as described earlier for the compound of formula VI. The reaction between the compounds of formulae VII and VIII is carried out in exactly the same manner that is used for the reaction of a compound of formula VI with a compound of formula III. Finally, any amino and/or carboxy protecting groups are removed, and these are removed in conventional manner for the group involved.

As will be appreciated by one skilled in the art, the group $R^2$ in the compound of formula VIII can contain a pro-amino group of the type referred to earlier in this specification, and said pro-amino group can be converted into an amino group after reaction of the compound of formula VII with the compound of formula VIII.

In another method according to the invention, a compound of formula I can be prepared by acylation of the compound of formula II with an activated derivative of an acid of the formula $R^2$—COOH, wherein $R^2$ is as previously defined, followed if necessary by removal of any amino and/or carboxy protecting groups from $R^2$. This converts the moiety $R^2$—CO into the moiety $R^1$—CO. Additionally the group $R^2$ in the carboxylic acid of formula $R^2$—COOH can contain a pro-amino group of the type referred to earlier in this specification, and said pro-amino group can be converted into an amino group after acylation of the compound of formula II with the acid of formula $R^2$—COOH.

The acylation reaction is usually conducted in a reaction-inert solvent system. In a typical acylation procedure, from about 0.5 to about three molar equivalents of the activated derivative of the acid of formula $R^2$—COOH is contacted with the compound of formula II, in a reaction-inert solvent system, at a temperature in the range from about $-40°$ to about 30° C., and preferably from about $-10°$ to about 10° C. The preferred ratio of activated derivative to compound of formula II is 1.0:1.0 to 1.2:1.0. Reaction-inert solvents which are commonly used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone; tertiary amides, such as N,N-dimethylformamide and N-methylpyrrolidone; acetonitrile; water; and mixtures thereof. When aqueous or partially aqueous solvent systems are used, the pH should be maintained in the range from about 4 to about 9, and preferably about 7.

An activated derivative of the acid of the formula $R^2$—COOH which is commonly used is an acid halide, e.g. the acid chloride. In this instance it is preferable, though not essential, to carry out the acylation in the presence of an acid binder. Suitable acid binders are tertiary amines such as trialkylamines, e.g. triethylamine, N-methylmorpholine, N,N-dimethylaniline, pyridine and the like, or bicarbonates such as potassium bicarbonate or sodium bicarbonate. Buffer systems such as phosphate buffers can also be used.

Other activated derivatives of the acid of formula $R^2$—COOH which can be used are active esters. Examples of active esters are phenyl esters, such as 4-nitrophenyl and 2,4,5-trichlorophenyl esters; thio esters, such as thiol methyl and thiol phenyl esters; and N-hydroxy esters, such as N-hydroxysuccinimide and N-hydroxyphthalimide esters. These active esters are prepared by methods well-known in the art. In many cases, the active ester can be replaced by the corresponding acid azide, or by the imidazole or triazole amide.

Another method for activation of the acid of formula $R^2$—COOH involves mixed anhydride formation, i.e. mixed carboxylic-carbonic and mixed dicarboxylic anhydride formation. In the case of mixed carboxylic carbonic anhydrides, a carboxylate salt of the acid of formula $R^2$—COOH is usually reacted with a lower-alkyl chloroformate, e.g. ethyl chloroformate; in the case of a mixed dicarboxylic anhydride, a carboxylate salt of the acid of formula $R^2$—COOH is usually reacted with a hindered lower-alkanoyl chloride, e.g. pivaloyl chloride.

In addition to the above, the acid of formula R²—COOH can be activated by contacting the acid with a peptide coupling agent, according to standard procedures. Such agents include carbodiimides, for example dicyclohexylcarbodiimide, alkoxyacetylenes, for example methoxyacetylene and ethoxyacetylene, and N-ethoxycarbonyl-2-ethoxy-1,2-dihydroquinoline.

The protecting groups used to protect amino or carboxy groups in a compound of formula R²—COOH are those conventionally used during acylation of a 6-aminopenicillanic acid derivative. Protecting groups which are particularly useful for amino groups are the benzyloxycarbonyl group, the 4-nitrobenzyloxycarbonyl group and the enamines formed by condensation with a beta-dicarbonyl compound such as an alkyl acetoacetate. After the acylation step, the amino protecting group is removed in conventional fashion. When the acid of formula R²—COOH is to be activated as an acid halide e.g. acid chloride, an especially convenient manner of protecting an amino group involves salt formation, e.g. formation of a hydrochloride salt.

The compounds of formula VI are known antibiotics, which are prepared by the published procedures.

The compounds of formula III are prepared from the compounds of formula VII by reaction with a compound of formula Y—CH(Q)—X, wherein X and Y are each good leaving groups, e.g. chloro, bromo, iodo, alkylsulfonyloxy, phenylsulfonyloxy or tolylsulfonyloxy, and Q is as defined previously. The same conditions that were described previously for reaction of a compound of formula III with a compound of formula VI are used for this reaction, except that it is preferable to use an excess of the compound of formula Y—CH(Q)—X (e.g. at least a four-fold excess).

In like manner, the compounds of formula VIII are prepared by reaction of a compound of formula

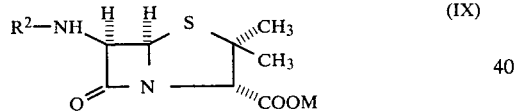

with a compound of formula Y—CH(Q)—X, wherein R², Q, M, Y and X are as previously defined. The conditions used are the same as those described previously for reaction of a compound of formula VII with a compound of formula Y—CH(Q)—X.

The compound of formula II can be prepared by a three-step procedure which comprises: (a) conversion of 6-aminopenicillanic acid into a 6-(protected amino)-penicillanic acid; (b) reaction of a salt of the 6-(protected amino)penicillanic acid with a compound of formula III; and (c) removal of the amino protecting group. A wide variety of amino protecting groups can be used for this purpose, and typical examples are benzyloxycarbonyl, 4-nitrobenzyloxycarbonyl and 2,2,2-trichloroethoxycarbonyl. Steps (a) and (c) are carried out in conventional fashion, and step (b) is carried out in exactly the same manner that was described previously for reaction of a compound of formula III with a compound of formula VI.

Alternatively, the compound of formula II can be prepared by a four-step procedure which comprises (i) conversion of 6-aminopenicillanic acid into a 6-(protected amino)penicillanic acid; (ii) reaction of a salt of the 6-(protected amino)penicillanic acid with a compound of formula X—CH(Q)—Y, wherein Q, X and Y are as previously defined; (iii) reaction of the product of step (ii) with a compound of formula VII; and (iv) removal of the amino protecting group. A wide variety of amino protecting groups can be used for this purpose, and typical examples are benzyloxycarbonyl, 4-nitrobenzyloxycarbonyl and 2,2,2-trichloroethoxycarbonyl. Steps (i) and (iv) are carried out in conventional fashion; step (ii) is carried out in exactly the same manner that was described previously for reaction of a compound of formula VII with a compound of formula X—CH(Q)—Y; and step (iii) is carried out in exactly the same manner that was described previously for reaction of a compound of formula VI with a compound of formula III.

The free acid corresponding to formula VII can be prepared by a three-step procedure from a penicillanic acid 1-alpha-oxide of formula X, as follows:

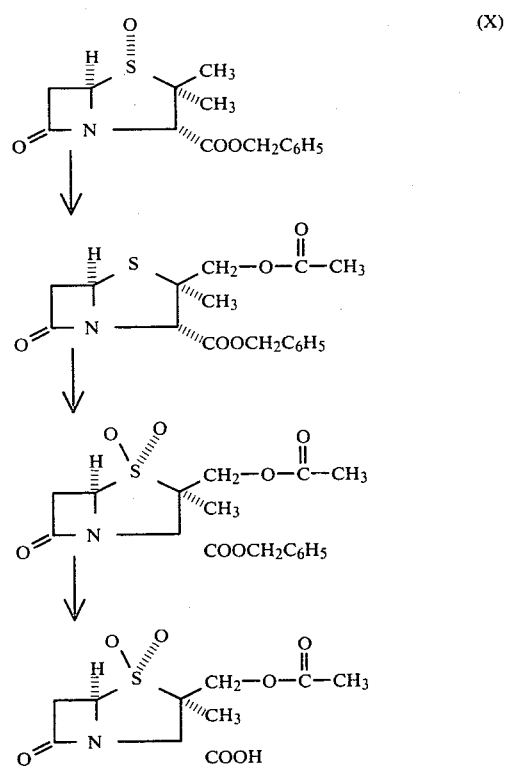

The first step of the above-depicted sequence can be carried out by heating the compound of formula X with acetic anhydride in toluene; the second step can be carried out using 3-chloroperbenzoic acid in chloroform; and the third step can be carried out by catalytic hydrogenolysis. The salts of formula VII are prepared from the free acid by conventional methods.

Benzyl penicillanate 1-alpha-oxide is prepared by published procedures (see U.S. Pat. No. 4,234,579).

Those compounds of formula I which have a basic function, e.g. an amino group, in the group R¹ will form acid addition salts, and these acid addition salts are considered to be within the scope and purview of this invention. Said acid addition salts are prepared by standard methods for penicillin compounds, for example by combining a solution of the compound of formula I in a suitable solvent (e.g. water, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate and 4-toluenesulfonate salts.

Those compounds of formula I which have an acidic function, e.g. a carboxyl group, in the group $R^1$ will form base salts, and these base salts are to be considered within the scope and purview of this invention. The base salts are prepared by standard methods for penicillin compounds, for example by contacting the acidic and basic components in a stoichiometric ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine, piperidine and N,N'-dibenzylethylenediamine; tertiary amines, such as triethylamine, N,N-dimethylaniline, N-ethylpiperidine, N-methylmorpholine, 2-(N,N-diethylamino)ethyl 4-aminobenzoate and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of formula I possess in vivo antibacterial activity in mammals, and this activity can be demonstrated by standard techniques for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula I. The compounds of formula I can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects. In general, it is the substitutent $R^1$ which determines whether a given bacterium will be susceptible to a given compound of formula I. A compound of formula I breaks down to the corresponding compound of formula VI (or free acid thereof) and 2-beta-acetoxymethyl-2-alpha-methyl-(5R)penam-3-alpha-carboxylic acid 1,1-dioxide after administration to a mammalian subject by both the oral and parenteral route. 2-beta-Acetoxymethyl-2-alpha-methyl(5R)penam-3-alpha-carboxylic acid 1,1-dioxide then functions as a beta-lactamase inhibitor, and it increases the antibacterial effectiveness of the compound of formula VI (or free acid thereof). For example, when $R^1$ is 2-phenylacetyl or 2-phenoxyacetyl, the compounds will find use in the control of infections caused by susceptible strains of *Staphylococcus aureus;* when $R^1$ is D-2-amino-2-phenylacetyl, D-2-amino-2-[4-hydroxyphenyl]acetyl or 2-carboxy-2-phenylacetyl, the compounds are useful in the control of infections caused by susceptible strains of *Escherichia coli.*

In determining whether a particular strain of *Staphylococcus aureus* or *Escherichia coli* is sensitive to a particular compound of formula I, the in vivo test described earlier can be used. Alternatively, the minimum inhibitory concentration (MIC) of a 1:1 mixture of the compound of formula VI (or its corresponding free acid) and the compound of formula VII (or its corresponding free acid) can be measured. The MIC's can be measured by the procedure recommended by the International Collaborative Study on Antibiotic Sensitivity Testing (Ericcson and Sherris, *Acta. Pathologica et Microbiologia Scandinav,* Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following Examples are provided solely for further illustration. Infrared spectra (IR spectra) were measured either neat, as a KBr disc or as nujol mulls, and diagnostic absorptions are reported in wave numbers (cm$^{-1}$). Nuclear magnetic resonance spectra (NMR spectra) were measured at 60 MHz in deuterochloroform (CDCl$_3$) or perdeutero dimethyl sulfoxide (DMSO-d$_6$), and absorptions are reported in parts per million (ppm) downfield from internal tetramethylsilane. The following abbreviations for peak shapes are used: s, singlet; broad s, broad singlet; d, doublet; q, quartet; m, multiplet.

EXAMPLE 1

6'-(2-Phenylacetamido)penicillanoyloxymethyl 2-beta-Acetoxymethyl-2-alpha-methyl-(5R)penam-3-alpha-carboxylate 1,1-Dioxide To a stirred solution of 1.3 g. of potassium 6-(2-phenylacetamido)penicillanate in 20 ml. of dimethyl sulfoxide is added 1.02 g. of chloromethyl 2-beta-acetoxymethyl-2-alpha-methyl-(5R)penam-3-alpha-carboxylate 1,1-dioxide followed by a few milligrams of sodium iodide. Stirring is continued overnight at ca. 25° C., and then the reaction mixture is poured into 140 ml. of ice-water. The pH is raised to 8.5, and then the mixture is extracted with ethyl acetate. The combined ethyl acetate extracts are washed with water, dried (Na$_2$SO$_4$) and evaporated in vacuo. This affords the crude title compound. It can be purified by chromatography on silica gel, eluting with a mixture of ethyl acetate and hexane.

EXAMPLE 2

1-[6'-(2-Phenylacetamido)penicillanoyloxy]ethyl 2-beta-Acetoxymethyl-2-alpha-methyl-(5R)penam-3-alpha-carboxylate 1,1-Dioxide Reaction of potassium 6-(2-phenylacetamido)penicillanate with 1-chloroethyl 2-beta-acetoxymethyl-2-alpha-methyl-(5R)penam-3-alpha-carboxylate 1,1-dioxide, according to the procedure of Example 1, affords the title compound.

EXAMPLE 3

6'-(2-Phenoxyacetamido)penicillanoyloxymethyl 2-beta-Acetoxymethyl-2-alpha-methyl-(5R)penam-3-alpha-carboxylate 1,1-Dioxide Reaction of potassium 6-(2-phenoxyacetamido)penicillanate with chloromethyl 2-beta-acetoxymethyl-2-alpha-methyl-(5R)penam-3-alpha-carboxylate 1,1-dioxide, according to the procedure of Example 1, affords the title compound.

EXAMPLE 4

1-[6'-(2-Phenoxyacetamido)penicillanoyloxy]ethyl 2-beta-Acetoxymethyl-2-alpha-methyl-(5R)penam-3-alpha-carboxylate 1,1-Dioxide Reaction of potassium 6-(2-phenoxyacetamido)penicillanate with 1-chloroethyl 2-beta-acetoxymethyl-2-alpha-methyl-(5R)penam-3-alpha-carboxylate 1,1-dioxide, according to the procedure of Example 1, affords the title compound.

EXAMPLE 5

6'-(2-Amino-2-phenylacetamido)penicillanoyloxymethyl 2-beta-Acetoxymethyl-2-alpha-methyl-(5R)penam-3-alpha-carboxylate 1,1-Dioxide A mixture of 4.5 g. of 6'-(2-azido-2-phenylacetamido)penicillanoyloxymethyl 2-beta-acetoxymethyl-2-alpha-methyl-(5R)penam-3-alpha-carboxylate 1,1-dioxide, 4.5 g. of 10% palladium-on-carbon, 30 ml. of dichloromethane and 30 ml. of isopropanol was shaken under an atmosphere of hydrogen, at ca. 50 psig, for 1 hour. An additional 1.0 g. of 10% palladium-on-carbon was then added and the shaking under hydrogen at ca. 50 psig was continued for 30 minutes. The reaction mixture was then filtered and the filtrate was evaporated to dryness in vacuo. The residue was triturated under ether, to give 3.35 g. of the title compound. The IR spectrum (nujol mull) showed absorptions at 1790 and 1780 cm$^{-1}$. The NMR spectrum (DMSO-d$_6$) showed absorptions at 1.36 (s, 3H), 1.5 (broad s, 6H), 2.1 (s, 3H), 3.0–3.9 (m, 2H), 4.42 (s, 1H), 4.5 (broad s, 2H), 4.8–5.1 (m, 3H), 5.38–5.7 (m, 2H), 5.95 (broad s, 2H), 5.0–7.0 (m, 2H), 7.42 (broad s, 5H), and 8.8–9.7 (m, 1H) ppm. On attempted melting point determination, the material decomposed at ca. 90° C.

EXAMPLE 6

6'-(2-Amino-2-phenylacetamido)penicillanoyloxymethyl 2-beta-Acetoxymethyl-2-alpha-methyl-(5R)penam-3-alpha-carboxylate 1,1-Dioxide Hydrochloride A 3.15 g. sample of the product of Example 5 was added portionwise to 48 ml. of ice-cold 0.1 N hydrochloric acid, during 2 minutes, with stirring. Stirring was continued for a further 5 minutes, and then the mixture was lyophilized. This afforded 3.15 g. of the title salt as a fluffy white solid. The IR spectrum (nujol mull) showed absorptions at 1790 and 1775 cm$^{-1}$. The NMR spectrum (DMSO-d$_6$) showed absorptions at 1.3 (s, 3H), 1.47 (broad s, 6H), 2.08 (s, 3H), 3.0–3.9 (m, 2H), 4.4 (s, 1H), 4.47 (broad s, 2H), 4.9 (s, 1H), 5.0–5.18 (m, 2H), 5.3–5.62 (m, 2H), 5.88 (broad s, 2H), 7.4 (broad s, 5H), 8.6–9.6 (broad s, 3H) and 9.55 (d, 1H) ppm.

EXAMPLE 7

1-[6'-(2-Amino-2-phenylacetamido)penicillanoyloxy]ethyl 2-beta-Acetoxymethyl-2-alpha-methyl-(5R)penam-3-alpha-carboxylate 1,1-Dioxide The title compound is prepared by reduction of 1-[6'-(2-azido-2-phenylacetamido)penicillanoyloxy]ethyl 2-beta-acetoxymethyl-2-alpha-methyl-(5R)penam-3-alpha-carboxylate 1,1-dioxide according to the procedure of Example 5.

EXAMPLE 8

6'-(2-Amino-2-[4-hydroxyphenyl]acetamido)penicillanoyloxymethyl 2-beta-Acetoxymethyl-2-alpha-methyl-(5R)penam-3-alpha-carboxylate 1,1-Dioxide A mixture of 1.3 g. of 6'-(2-benzyloxycarbonylamino-2-[4-hydroxyphenyl]acetamido)penicillanoyloxymethyl 2-beta-acetoxymethyl-2-alpha-methyl-(5R)penam-3-alpha-carboxylate 1,1-dioxide (from Preparation 3), 0.7 g. of 6'-(2-benzyloxycarbonylamino-2-[4-benzyloxycarbonyloxyphenyl]acetamido)penicillanoyloxymethyl 2-beta-acetoxymethyl-2-alpha-methyl-(5R)penam-3-alpha-carboxylate 1,1-dioxide (from Preparation 3), 30 ml. of dichloromethane, 30 ml. of isopropanol and 2.0 g. of 10% palladium-on-carbon was shaken under an atmosphere of hydrogen, at ca. 50 psig, for 45 minutes. At this point, a further 2.0 g. of 10% palladium-on-carbon was added and the mixture was shaken under hydrogen, at ca. 50 psig, for a further 45 minutes. The step of adding an additional 2.0 g. of 10% palladium-on-carbon and rehydrogenation for 45 minutes was repeated 3 more times. The reaction mixture was then filtered and the filtrate was evaporated to dryness in vacuo. The residue was triturated under ether, and this afforded 0.97 g. of the title compound. The IR spectrum of the product (nujol mull) showed a broad absorption at 1805–1725 cm$^{-1}$. The NMR spectrum of the product (DMSO-d$_6$) showed absorptions at 1.38 (s, 3H), 1.4 (s, 3H), 1.5 (s, 3H), 2.05 (s, 3H), 3.0–3.95 (m, 2H), 4.38 (s, 1H), 4.44 (broad s, 2H), 4.88–5.0 (m, 2H), 5.04–5.2 (m, 1H), 5.32–5.63 (m, 2H), 5.88 (broad s, 2H), 6.72 (d, 2H), 7.22 (d, 2H), 8.4–9.2 (broad s, 2H), 9.42 (d, 1H) and 10.0 (broad s, 1H) ppm.

EXAMPLE 9

6'-(2-Amino-2-[4-hydroxyphenyl]acetamido)penicillanoyloxymethyl 2-beta-Acetoxymethyl-2-alpha-methyl-(5R)penam-3-alpha-carboxylate 1,1-Dioxide Hydrochloride The product of Example 8 (0.97 g.) was added to 13.8 ml. of 0.1 N hydrochloric acid at 0° C., and the mixture was stirred until a solution was obtained. The solution was then lyophilized to give 0.89 g. of the title salt. The IR spectrum of the title salt showed a broad absorption at 1805 to 1725 cm$^{-1}$. The NMR spectrum of the title salt (DMSO-d$_6$) showed absorptions at 1.32 (s, 3H), 1.42 (s, 3H), 1.45 (s, 3H), 2.02 (s, 3H), 3.0–3.9 (m, 2H), 4.35 (s, 1H), 4.42 (broad s, 2H), 4.8–5.2 (m, 3H), 5.26–5.6 (m, 2H), 5.83 (broad s, 2H), 6.7 (d, 2H), 7.2 (d, 2H), 8.6–9.3 (broad s, 3H) and 9.5 (d, 2H) ppm.

EXAMPLE 10

The procedure of Example 1 is repeated, except that the chloromethyl 2-beta-acetoxymethyl-2-alpha-methyl-(5R)penam-3-alpha-carboxylate 1,1-dioxide is replaced by an equimolar amount of:

bromomethyl 2-beta-acetoxymethyl-2-alpha-methyl-(5R)penam-3-alpha-carboxylate 1,1-dioxide, iodomethyl 2-beta-acetoxymethyl-2-alpha-methyl-(5R)penam-3-alpha-carboxylate 1,1-dioxide, methylsulfonyloxymethyl 2-beta-acetoxymethyl-2-alpha-methyl-(5R)penam-3-alpha-carboxylate 1,1-dioxide, isobutylsulfonyloxymethyl 2-beta-acetoxymethyl-2-alpha-methyl-(5R)penam-3-alpha-carboxylate 1,1-dioxide, phenylsulfonyloxymethyl 2-beta-acetoxymethyl-2-alpha-methyl-(5R)penam-3-alpha-carboxylate 1,1-dioxide and 4-tolylsulfonyloxymethyl 2-beta-acetoxymethyl-2-alpha-methyl-(5R)penam-3-alpha-carboxylate 1,1-dioxide, respectively. In each case this affords 6'-(2-phenylacetamido)penicillanoyloxymethyl 2-beta-acetoxymethyl-2-alpha-methyl-(5R)penam-3-alpha-carboxylate 1,1-dioxide.

In like manner, the procedure of Example 1 is repeated, except that the chloromethyl 2-beta-acetoxymethyl-2-alpha-methyl-(5R)penam-3-alpha-carboxylate 1,1-dioxide is replaced by an equimolar amount of:

1-chloroethyl 2-beta-acetoxymethyl-2-alpha-methyl-(5R)penam-3-alpha-carboxylate 1,1-dioxide, 1-iodoethyl 2-beta-acetoxymethyl-2-alpha-methyl-(5R)penam-3-alpha-carboxylate 1,1-dioxide, 1-(methylsulfonyloxy)ethyl 2-beta-acetoxymethyl-2-alpha-methyl-(5R)penam-3-alpha-carboxylate 1,1-dioxide and 1-(3-tolylsulfonyloxy)ethyl 2-beta-acetoxymethyl-2-alpha-methyl-(5R)penam-3-alpha-carboxylate 1,1-dioxide, respectively. In each case this affords 1-[6'-(2-phenylacetamido)penicillanoyloxy]ethyl 2-beta-acetoxymethyl-2-alpha-methyl-(5R)penam-3-alpha-carboxylate 1,1-dioxide.

EXAMPLE 11

6'-(2-Carboxy-2-phenylacetamido)penicillanoyloxymethyl 2-beta-Acetoxymethyl-2-alpha-methyl-(5R)penam-3-alpha-carboxylate 1,1-Dioxide To a stirred solution of 2.60 g. of 6'-aminopenicillanoyloxymethyl 2-beta-acetoxymethyl-2-alpha-methyl-(5R)penam-3-alpha-carboxylate 1,1-dioxide in 15 ml. of ethyl acetate is added 0.605 g. of N,N-dimethylaniline at 0° C. The temperature is maintained at 0° C., and 30 ml. of a 0.2 molar solution of phenylmalonyl chloride trimethylsilyl ester is added dropwise during 5 minutes. The reaction mixture is washed with water, and then an equal volume of fresh water is added. The pH of the aqueous phase is adjusted to 7.0 with saturated sodium bicarbonate and the layers are separated. The organic layer is discarded, and fresh ethyl acetate is added to the aqueous layer. The pH of the aqueous layer is lowered to 3.5, and again the layers are separated. The ethyl acetate layer is dried (Na$_2$SO$_4$) and evaporated in vacuo to give the title compound.

The 0.2 molar solution of phenylmalonyl chloride trimethylsilyl ester is prepared according to Preparation A of U.S. Pat. No. 3,862,933.

EXAMPLE 12

1-[6'-(2-Carboxy-2-phenylacetamido)penicillanoyloxy]ethyl 2-beta-Acetoxymethyl-2-alpha-methyl-(5R)penam-3-alpha-carboxylate 1,1-Dioxide The title compound is prepared by acylation of 1-[6'-aminopenicillanoyloxy]ethyl 2-beta-acetoxymethyl-2-alpha-methyl-(5R)penam-3-alpha-carboxylate 1,1-dioxide with phenylmalonyl chloride trimethylsilyl ester, using the procedure of Example 11.

EXAMPLE 13

6'-Aminopenicillanoyloxymethyl 2-beta-Acetoxymethyl-2-alpha-methyl-(5R)penam-3-alpha carboxylate 1,1-Dioxide To a solution of 1.2 g. of 6'-(4-nitrobenzyloxycarbonylamino)penicillanoyloxymethyl 2-beta-acetoxymethyl-2-alpha-methyl-(5R)penam-3-alpha-carboxylate 1,1-dioxide in a mixture of 30 ml. of water and 50 ml. of tetrahydrofuran is added 1 drop of acetic acid, followed by 1.2 g. of 10% palladium-on-carbon. The mixture is shaken under an atmosphere of hydrogen, at ca. 50 psig pressure, for 1.5 hours. The mixture is then filtered and the residue is washed with water and with tetrahydrofuran. The tetrahydrofuran-water, water and tetrahydrofuran solutions are combined and the pH is adjusted to 8.5. The resulting solution is extracted with ethyl acetate, and the ethyl acetate extract is dried ($Na_2SO_4$). The dried solution is evaporated in vacuo giving the title product.

This material can be purified by chromatography on silica gel, eluting with ethyl acetate-hexane.

6'-Aminopenicillanoyloxymethyl 2-beta-acetoxymethyl-2-alpha-methyl-(5R)penam-3-alpha-carboxylate 1,1-dioxide will form acid-addition salts. The salts are prepared in conventional fashion, i.e. using the methods described earlier for the formation of acid-addition salts of those compounds of formula I which have an amino group as part of the group $R^1$.

EXAMPLE 14

1-[6'-Aminopenicillanoyloxy]ethyl 2-beta-Acetoxymethyl-2-alpha-methyl-(5R)penam-3-alpha-carboxylate 1,1-Dioxide The title compound is prepared by hydrogenolysis of 1-[6'-(4-nitrobenzyloxycarbonylamino)penicillanoyloxy]ethyl 2-beta-acetoxymethyl-2-alpha-methyl-(5R)penam-3-alpha-carboxylate 1,1-dioxide, using the procedure of Example 13.

EXAMPLE 15

Chloromethyl 2-beta-Acetoxymethyl-2-alpha-methyl-(5R)penam-3-alpha-carboxylate 1,1-Dioxide To a stirred mixture of 10.0 g. of 2-beta-acetoxymethyl-2-alpha-methyl-(5R)penam-3-alpha-carboxylic acid 1,1-dioxide, 75 ml. of dichloromethane and 25 ml. of water, was added 40% aqueous tetrabutylammonium hydroxide until the pH rose to 6.0. The layers were separated, and the aqueous phase was extracted with further dichloromethane. The combined dichloromethane solutions were dried ($Na_2SO_4$) and concentrated in vacuo to give 19.0 g. of the tetrabutylammonium salt of 2-beta-acetoxymethyl-2-alpha-methyl-(5R)penam-3-alpha-carboxylic acid, as an amber oil. The NMR spectrum of this oil ($CDCl_3$) showed absorptions at 0.75–2.0 (m, 26H), 1.65 (s, 3H), 2.07 (s, 3H), 3.0–3.6 (m, 10H), 4.08 (s, 1H) and 4.35–4.82 (m, 3H) ppm.

The above tetrabutylammonium salt and 50 ml. of chloroiodomethane were stirred at room temperature for ca. 18 hours, and then the reaction mixture was concentrated in vacuo. The residue was chromatographed on 300 g. of silica gel using 1:1 ethyl acetate-hexane. The product containing fractions were combined and evaporated in vacuo, giving 4.0 g. of the title ester as a viscous oil. The IR spectrum of the product (neat) showed an absorption at 1790 $cm^{-1}$. The NMR spectrum of the product ($CDCl_3$) showed absorptions at 1.5 (s, 3H), 2.1 (s, 3H), 3.45 (m, 2H), 4.23–4.7 (m, 4H) and 5.72 (q, 2H) ppm.

EXAMPLE 16

The procedure of Example 15 is repeated, except that the chloroiodomethane used therein is replaced by an equimolar amount of bromoiodomethane, diiodomethane, di(methylsulfonyloxy)methane, di(isobutylsulfonyloxy)methane, di(phenylsulfonyloxy)methane, di(4-tolylsulfonyloxy)methane, 1-chloro-1-iodoethane, 1,1-diiodoethane, 1,1-di(methylsulfonyloxy)ethane, and 1,1-di(3-tolylsulfonyloxy)ethane. This affords:

bromomethyl 2-beta-acetoxymethyl-2-alpha-methyl-(5R)penam-3-alpha-carboxylate 1,1-dioxide, iodomethyl 2-beta-acetoxymethyl-2-alpha-methyl-(5R)penam-3-alpha-carboxylate 1,1-dioxide, methylsulfonyloxmethyl 2-beta-actoxymethyl-2-alpha-methyl-(5R)penam-3-alpha-carboxylate 1,1-dioxide, isobutylsulfonyloxymethyl 2-beta-acetoxymethyl-2-alpha-methyl-(5R)penam-3-alpha-carboxylate 1,1-dioxide, phenylsulfonyloxymethyl 2-beta-acetoxymethyl-2-alpha-methyl-(5R)penam-3-alpha-carboxylate 1,1-dioxide, 4-tolylsulfonyloxymethyl 2-beta-acetoxymethyl-2-alpha-methyl-(5R)penam-3-alpha-carboxylate 1,1-dioxide, 1-chloroethyl 2-beta-acetoxymethyl-2-alpha-methyl-(5R)penam-3-alpha-carboxylate 1,1-dioxide, 1-iodoethyl 2-beta-acetoxymethyl-2-alpha-methyl-(5R)penam-3-alpha-carboxylate 1,1-dioxide, 1-(methylsulfonyloxy)ethyl 2-beta-acetoxymethyl-2-alpha-methyl-(5R)penam-3-alpha-carboxylate 1,1-dioxide, 1-(3-tolylsulfonyloxy)ethyl 2-beta-acetoxymethyl-2-alpha-methyl-(5R)penam-3-alpha-carboxylate 1,1-dioxide, respectively.

EXAMPLE 17

Iodomethyl 2-beta-Acetoxymethyl-2-alpha-methyl-(5R)penam-3-alpha-carboxylate 1,1-Dioxide A mixture of 3.9 g. of chloromethyl 2-beta-acetoxymethyl-2-alpha-methyl-(5R)penam-3-alpha-carboxylate 1,1-dioxide, 8.6 g. of sodium iodide and 30 ml. of acetone was stirred overnight, and then it was evaporated in vacuo. The residue was dissolved in 50 ml. of ethyl acetate and the solution was washed with water followed by saturated sodium chloride solution. The ethyl acetate solution was then dried ($Na_2SO_4$) and evaporated in vacuo. The residue was chromatographed on 150 g. of silica gel, using 1:1 ethyl acetate-hexane. The product containing fractions were combined and evaporated in vacuo to give 4.24 g. of the title ester as an oil. The IR spectrum of the product (neat) showed a broad absorption at 1790 to 1785 cm$^{-1}$. The NMR spectrum of the product (CDCl$_3$) showed absorptions at 1.55 (s, 3H), 2.1 (s, 3H), 3.47 (d, 2H), 4.23–4.68 (m, 4H) and 5.94 (q, 2H) ppm.

PREPARATION 1

6'-(2-Azido-2-phenylacetamido)penicillanoyloxymethyl 2beta-Acetoxymethyl-2-alpha-methyl-(5R)penam-3-alpha-carboxylate 1,1-Dioxide A mixture of 6.16 g. of the tetrabutylammonium salt of 6-(2-azido-2-phenylacetamido)penicillanate (prepared from the free acid and tetrabutylammonium hydroxide), 4.1 g. of chloromethyl 2-beta-acetoxymethyl-2-alpha-methyl-(5R)penam-3-alpha-carboxylate 1,1-dioxide and 40 ml. of acetone was stirred until solution took place (ca. 3 minutes), and then for an additional 30 minutes. The solvent was removed by evaporation in vacuo and 50 ml. of dichloromethane was added to the residue. The solid which remained out of solution was removed by filtration and then the dichloromethane solution evaporated in vacuo. The residue which remained was chromatographed on 600 g. of silica gel using 80:20 dichloromethane-ethyl acetate. The product-containing fractions were combined to give 4.7 g. of the title compounds as a yellow foam. The IR spectrum of the product (nujol mull) showed absorptions at 1790 and 1775 cm$^{-1}$. The NMR spectrum of the product (CDCl$_3$) showed absorptions at 1.45 (s, 3H), 1.5 (s, 3H), 1.62 (s 3H), 3.42 (d, 2H), 4.22–4.7 (m, 5H), 5.07 (s, 1H), 5.42–5.7 (m, 2H), 5.83 (s, 2H), 7.1 (d, 1H) and 7.35 (s, 5H) ppm.

PREPARATION 2

1-[6'-(2-Azido-2-phenylacetamido)penicillanoyloxy]ethyl 2-beta-Acetoxymethyl-2-alpha-methyl-(5R)penam-3-alpha-carboxylate 1,1-Dioxide Reaction of the tetrabutylammonium salt of 6-(2-azido-2-phenylacetamido)penicillanate with 1-chloroethyl 2-beta-acetoxymethyl-2-alpha-methyl-(5R)penam-3-alpha-carboxylate 1,1-dioxide, according to the Procedure of Preparation 1, but with a reaction time of 16 hours, affords the title compound.

PREPARATION 3

Reaction of Benzyloxycarbonyl-protected 6-(2-Amino-2-[4-hydroxyphenyl]acetamidopenicillanic Acid with Chloromethyl 2-beta-Acetoxymethyl-2-alpha-methyl-(5R)penam-3-alpha-carboxylate 1,1-Dioxide To a stirred mixture of 5.0 g. of the product of Preparation 4, 75 ml. of dichloromethane and 25 ml. of water was added 40% aqueous tetrabutylammonium hydroxide, until a stable pH of 8.0 was achieved. The layers were separated and the aqueous layer was washed with dichloromethane. The combined dichloromethane solutions were evaporated in vacuo to give 7.9 g. of a yellow foam.

A mixture of the above 7.9 g. of yellow foam, 2.15 g. of iodomethyl 2-beta-acetoxymethyl-2-alpha-methyl-(5R)penam-3-alpha-carboxylate 1,1-dioxide and 30 ml. of acetone was stirred for 5 minutes. Examination of the reaction mixture at this point indicated the absence of starting material and the presence of two products. The reaction medium was evaporated in vacuo, and the residue was chromatographed on 500 g. of silica gel, eluting with 60:40 ethyl acetatedichloromethane.

The fractions containing the less polar product were combined and evaporated in vacuo to give 0.7 g. of a yellow foam. NMR spectroscopy showed this material to be 6'-(2-[benzyloxycarbonylamino]-2-[4-benzyloxycarbonyloxyphenyl]acetamido)penicillanoyloxymethyl 2-beta-acetoxymethyl-2-alpha-methyl-(5R)penam-3-alpha-carboxylate 1,1-dioxide.

The fractions containing the more polar product were combined and evaporated in vacuo to give 1.3 g. of a pale yellow foam. NMR spectroscopy showed this material to be 6'-(2-[benzyloxycarbonylamino]-2-[4-hydroxyphenyl]acetamido)penicillanoyloxymethyl 2-beta-acetoxymethyl-2-alpha-methyl-(5R)penam-3-alpha-carboxylate 1,1-dioxide.

PREPARATION 4

Benzyloxycarbonyl Protection of 6-(2-Amino-2-[4-hydroxyphenyl]acetamido)penicillanic Acid To a stirred slurry of 39.0 g. of 6-(2-amino-2-[4-hydroxyphenyl]acetamido)penicillanic acid trihydrate in 500 ml. of water and 300 ml. of acetone was added 6 N sodium hydroxide to give a stable pH of 8.2. To the solution so obtained was added 13.6 ml. of benzyloxycarbonyl chloride, dropwise, with stirring, during 30 minutes, with the pH being maintained between 7.0 and 8.0 by the simultaneous addition of 6 N sodium hydroxide. Stirring and addition of sodium hydroxide was continued until the pH stabilized at 7.5, and then the mixture was extracted three times with ether. To the aqueous phase was added 300 ml. of ethyl acetate, and the pH was lowered to 2.0. The ethyl acetate layer was removed, and the aqueous phase was further extracted with ethyl acetate. The combined ethyl acetate solutions were washed with water, dried (Na$_2$SO$_4$) and concentrated in vacuo to give 47.2 g of a foam. Examination of this product showed that it was 6-(2-benzyloxycarbonylamino-2-[4-hydroxyphenyl]acetamido)-penicillanic acid, contaminated with some 6-(2-benzyloxycarbonylamino-2-[4-benzyloxycarbonyloxyphenyl]acetamido)penicillanic acid.

PREPARATION 5

6'-(4-Nitrobenzyloxycarbonylamino)penicillanoyloxymethyl 2-beta-Acetoxymethyl-2-alpha-methyl-(5R)penam-3-alpha-carboxylate 1,1-Dioxide To a stirred solution of 4.32 g. of potassium 6-(4-nitrobenzyloxycarbonylamino)penicillanate in 60 ml. of dimethyl sulfoxide is added 3.05 g. of chloromethyl 2-beta-acetoxymethyl-2-alpha-methyl-(5R)penam-3-alpha-carboxylate 1,1-dioxide, followed by a few milligrams of sodium iodide. Stirring is continued for 16 hours, and then the mixture is poured in 200 ml. of water. The pH is adjusted to 8.5, and the resulting mixture is extracted with ethyl acetate. The ethyl acetate extracts are washed with water followed by saturated sodium chloride solution. The resulting solution is evaporated in vacuo to give the title compound. It can be purified by chromatography on silica gel, eluting with ethyl acetate.

PREPARATION 6

1-[6'-(4-Nitrobenzyloxycarbonylamino)penicillanoyloxy]ethyl 6-beta-Acetoxymethyl-6-alpha-methyl-(5R)penam-3-alpha-carboxylate 1,1-Dioxide The title compound is prepared from potassium 6-(4-nitrobenzyloxycarbonylamino)penicillanate and 1-chloroethyl 6-beta-acetoxymethyl-6-alpha-methyl-(5R)penam-3-alpha-carboxylate 1,1-dioxide, using the method of Preparation 5.

PREPARATION 7

2-beta-Acetoxymethyl-2-alpha-methyl-(5R)penam-3-alpha-carboxylic Acid 1,1-Dioxide To a solution of 84.5 g. of benzyl 2-beta-acetoxymethyl-2-alpha-methyl-(5R)penam-3-alpha-carboxylate 1,1-dioxide in 1.1 liters of ethyl acetate was added 44 g. of 5% palladium-on-carbon. The mixture was shaken under an atmosphere of hydrogen at ca. 50 psig for 2 hours, and then the catalyst was removed by filtration.

The above filtrate was combined with the corresponding filtrate from a duplicate experiment, and the volume was reduced to 1.5 liters. To this solution was added, slowly, 1.7 liters of hexane. The volume was reduced to ca. 2 liters, and the solid which precipitated was recovered by filtration and slurried under hexane to give 98 g., (76% yield) of the title product. The NMR spectrum (CDCl$_3$+DMSO-d$_6$) showed absorptions at 1.65 (s, 3H), 2.15 (s, 3H), 3.55 (d, 2H) and 4.65 (m, 4H) ppm. The IR spectrum of the product (KBr disc) showed absorptions at 1785, 1330, 1225 and 1190 cm$^{-1}$.

Analysis: Calcd. for C$_{10}$H$_{13}$NO$_7$S: C, 41.2; H, 4.49; N, 4.80; S, 11.00%. Found: C, 41.34; H, 4.55; N, 4.81; S, 11.08%.

PREPARATION 8

Benzyl 2-beta-Acetoxymethyl-2-alpha-methyl-(5R)penam-3-alpha-carboxylate 1,1-Dioxide A stirred solution of 3.49 g. of benzyl 2-beta-acetoxymethyl-2-alpha-methyl-(5R)penam-3-alpha-carboxylate in 35 ml. of chloroform was cooled to 0° C., and 5 g. of 85% pure 3-chloroperbenzoic acid was added in two portions 15 minutes apart. The cooling bath was removed, and the mixture was stirred overnight without cooling. The reaction mixture was then cooled back to 0° C., and 70 ml. of water and 70 ml. of ethyl acetate were added. The organic layer was removed, and then it was washed successively with aqueous sodium sulfite solution, saturated aqueous sodium bicarbonate solution and saturated aqueous sodium chloride solution. The dried (Na$_2$SO$_4$) organic layer was evaporated in vacuo to give 4.8 g. of a brown oil, which slowly crystallized.

The above product was dissolved in 35 ml. of chloroform, and it was further oxidized using 5 g. of 85% 3-chloroperbenzoic acid for 19 hours. The reaction mixture was worked up as previously to give the crude title product. This crude product was dissolved in dichloromethane and the solution was washed with saturated aqueous sodium bicarbonate. Magnesium sulfate and decolorizing carbon were added to the dichloromethane solution, and then the filtered dichloromethane solution was evaporated in vacuo. This afforded 3.0 g. (79% yield) of the title compound. The NMR spectrum (CDCl$_3$) of the product showed absorptions at 1.25 (s, 3H), 2.00 (s, 3H), 3.40 (d, 2H), 4.55 (m, 4H), 5.15 (s, 2H) and 7.30 (s, 5H) ppm.

PREPARATION 9

Benzyl 2-beta-Acetoxymethyl-2-alpha-methyl-(5R)penam-3-alpha-carboxylate

A mixture of 68 ml. of acetic anhydride and 10 ml. of toluene was heated to 112° C. in a round bottom flask equipped with a distillation head and a condenser in the distillation position. When the temperature reached 112° C. liquid began to distil and then preheated toluene (ca. 100° C.) was added to the round bottom flask at the same rate that distillate was being collected. Slow distillation, and addition of preheated toluene, was continued for 20 minutes. At this point 10 g. of benzyl 2,2-dimethyl-(5R)penam-3-alpha-carboxylate 1-alpha-oxide was added to the liquid in the round bottom flask. A solution was obtained immediately. Slow distillation of the solution in the round bottom flask, and addition of preheated toluene, were continued for an additional 15 minutes. Throughout all this procedure, the temperature in the round bottom flask was maintained at 112° C. At this point the liquid in the round bottom flask was cooled to room temperature, and then it was evaporated in vacuo. This afforded a brown oil, which was partitioned between 100 ml. of ethyl acetate and 100 ml. of water. The pH of the aqueous phase was adjusted to 7.9 and the organic layer was removed. The organic layer was washed successively with water and saturated aqueous sodium chloride, and then it was dried and decolorized, using sodium sulfate and decolorizing carbon. Evaporation in vacuo gave 10.1 g. of crude title product.

PREPARATION 10

Benzyl 2-beta-Acetoxymethyl-2-alpha-methyl-(5R)penam-3-alpha-carboxylate

The procedure of Preparation 9 was repeated on a ten times scale, except that the internal temperature was maintained at 115° C. after the benzyl ester had been added, and the heating was continued for 1 hour after the benzyl ester had been added. The yield of crude title compound was 122 g.

The product of this example was combined with that from Preparation 9, and then it was chromatographed on 4 kg. of silica gel. The column was eluted with 1:9 ethyl acetate-chloroform, taking 500 ml. fractions. The chromatography was followed by thin-layer chromatography and several fractions were combined to give 3 major cuts. Cut 1 was 7.0 g. of an oil and it was discarded. Cut 2 was 67.5 g. of a solid which was substantially pure title product. Cut 3 was 21.7 g. of a solid which was also substantially pure title product. The combination of cut 2 and 3 represents a 72% yield.

Cut 2 was dissolved in 450 ml. of isopropyl alcohol at 60° C. The solution was allowed to cool slowly, and then the product was collected by filtration. The recovery of recrystallized material was 34.1 g. The NMR spectrum of this material (CDCl$_3$) showed absorptions at 1.30 (s, 3H), 2.10 (s, 3H), 3.05 (d of d, 1H), 3.55 (d of d, 1H), 4.05 (q, 2H), 4.80 (s, 1H), 5.20 (s, 2H), 5.30 (m, 1H) and 7.30 (s, 5H) ppm.

PREPARATION 11

Benzyl 2,2-Dimethyl-(5R)penam-3-alpha-carboxylate 1-alpha-Oxide

To a solution of 1756 g. of benzyl 6,6-dibromo-2,2-dimethyl-(5R)penam-3-alpha-carboxylate 1-alpha-oxide in 13.2 liters of tetrahydrofuran was added 9.4 liters of water, followed by 755 g. of potassium bicarbonate and 1756 g. of 5% palladium-on-calcium carbonate. This mixture was shaken under an atmosphere of hydrogen at ca. 50 psig for 1 hour. At this point the reaction mixture was diluted with 3.8 liters of ethyl acetate and 3.8 liters of water, and then it was filtered. The filter cake was washed with ethyl acetate and the ethyl acetate was added to the filtrate. The organic layer was removed, and then it was washed with 7 liters of water followed by 7 liters of saturated aqueous sodium chloride solution. The organic solution was dried using 450 g. of sodium sulfate and 280 g. of decolorizing carbon, and then it was evaporated in vacuo giving 833 g. (72% yield) of the title compound. The NMR spectrum (CDCl$_3$) showed absorptions at 1.35 (s, 3H), 1.60 (s, 3H), 3.50 (m, 2H), 4.50 (s, 1H), 4.65 (m, 1H), 5.25 (s, 2H) and 7.40 (s, 5H) ppm.

PREPARATION 12

Benzyl 6,6-Dibromo-2,2-dimethyl-(5R)penam-3-alpha-carboxylate 1-alpha-Oxide

A stirred solution of 1777 g. of benzyl 6,6-dibromo-2,2-dimethyl-(5R)penam-3-alpha-carboxylate in 7.5 liters of chloroform, under nitrogen, was cooled to 0° C. To this solution was then added, portionwise during 35 minutes, 796 g. of 85% pure 3-chloroperbenzoic acid. The temperature was maintained at 0° C. throughout the addition. Stirring was continued at 0° C. for 15 minutes, and then the reaction mixture was stirred overnight without cooling. At this point the solid which had precipitated was removed by filtration, and the chloroform solution was washed three times with 3.7 liters of 5% aqueous sodium hydroxide. To the chloroform solution was then added 126 g. of decolorizing carbon. The mixture was stirred for 10 minutes, and then the carbon was removed by filtration. The chloroform solution was washed successively with water and saturated aqueous sodium chloride solution, and then it was dried using sodium sulfate. The chloroform solution was evaporated in vacuo at 25° to 29° C., to give 1756 g. (95% yield) of the title compound.

The NMR spectrum (CDCl$_3$) of a sample of the title compound obtained from an analogous experiment showed absorptions at 1.35 (s, 3H), 1.60 (s, 3H), 4.65 (s, 1H), 1.15 (m, 3H), 4.65 (s, 1H), 1.15 (m, 3H) and 7.55 (s, 5H) ppm.

PREPARATION 13

Benzyl 6,6-Dibromo-2,2-dimethyl-(5R)penam-3-alpha-carboxylate

To a stirred solution of 1646 g. of 6,6-dibromo-2,2-dimethyl-(5R)penam-3-alpha-carboxylic acid in 10.1 liters of N,N-dimethylacetamide was added 709 ml. of triethylamine during 10 minutes at ca. 0° C. The temperature was adjusted to 10° C., and 602 ml. of benzyl bromide was added during 4 minutes. To the reaction mixture was then added 941 g. of 4A molecular sieves, and then the reaction mixture was stirred overnight without external cooling. At this point, the reaction mixture was filtered and the filtrate was added to a mixture of 44 liters of ice-water and 14 liters of ethyl acetate. The pH of the aqueous phase was adjusted to 2.0 using 6 N hydrochloric acid, and the layers were separated. The aqueous layer was extracted with further ethyl acetate and the combined ethyl acetate solutions were washed sequentially with 14 liters of saturated, aqueous sodium bicarbonate and 14 liters of saturated, aqueous sodium chloride. The ethyl acetate solution was dried (Na$_2$SO$_4$), and then it was evaporated in vacuo at 25° C. The residue was dissolved in 5.5 liters of isopropyl alcohol at 60° C., and then the isopropyl alcohol solution was cooled slowly with stirring. The solid which precipitated was recovered by filtration, washed with cold isopropyl alcohol and then air dried. This afforded 1777 g. (85% yield) of the title product. The NMR spectrum (CDCl$_3$) showed absorptions at 1.40 (s, 3H), 1.55 (s, 3H), 4.55 (s, 1H), 5.20 (s, 2H), 5.75 (s, 1H) and 7.35 (s, 5H) ppm.

A second crop weighing 110 g. was obtained from the isopropyl alcohol mother liquors.

PREPARATION 14

6'-(2-Benzyloxycarbonylamino-2-[4-hydroxyphenyl]acetamido)penicillanoyloxymethyl 2-beta-Acetoxymethyl-2-alpha-methyl-(5R)penam-3-alpha-carboxylate 1,1-Dioxide To a solution of 16.5 g. of 6-(2-benzyloxycarbonylamino-2-[4-hydroxyphenyl]acetamido)penicillanic acid in 150 ml. of ethyl acetate is added, with stirring, a solution of 5.5 g. of sodium 2-ethylhexanoate in ca. 50 ml. of ethyl acetate. Stirring is continued for 30 minutes, and then the precipitate is collected by filtration and washed with ethyl acetate. This affords sodium 6-(2-benzyloxycarbonyl-[4-hydroxyphenyl]acetamido)-penicillanate.

To a solution of 15.66 g. of sodium 6-(2-benzyloxycarbonyl-2-[4-hydroxyphenyl]acetamido)penicillanate in 50 ml. of N,N-dimethylformamide is added 11.64 g. of chloromethyl 2-beta-acetoxymethyl-2-alpha-methyl-(5R)penam-3-alpha-carboxylate 1,1-dioxide with stirring. Stirring is continued for 1 hour, and then the reaction mixture is diluted with 700 ml. of ethyl acetate and 700 ml. of water. The ethyl acetate layer is removed and washed with water, followed by 10% aqueous sodium carbonate, followed by saturated sodium chloride solution. The ethyl acetate solution is then dried (Na$_2$SO$_4$) and evaporated in vacuo to give the title compound.

I claim:

1. A compound of the formula

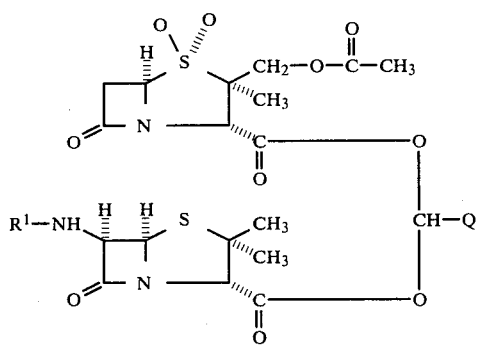

and the pharmaceutically-acceptable salts thereof, wherein $R^1$ is selected from the group consisting of 2-phenylacetyl, 2-phenoxyacetyl, 2-amino-2-phenylacetyl, 2-amino-2-[4-hydroxyphenyl]acetyl and 2-carboxy-2-phenylacetyl;

and Q is selected from the group consisting of hydrogen and methyl.

2. A compound according to claim 1, wherein Q is hydrogen.

3. The compound according to claim 2, wherein $R^1$ is 2-amino-2-phenylacetyl.

4. The compound according to claim 2, wherein $R^1$ is 2-amino-2-[4-hydroxyphenyl]acetyl.

5. A method of treating a bacterial infection in a mammalian subject, which comprises administering thereto, either orally or parenterally, an antibacterially effective amount of a compound of the formula

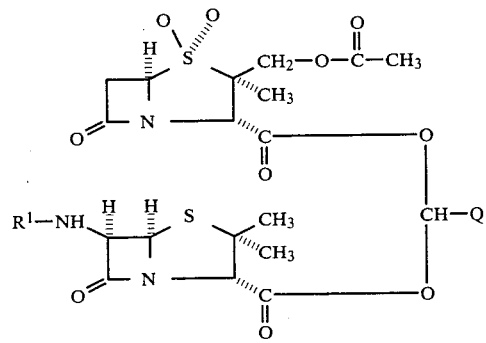

or a pharmaceutically-acceptable salt thereof,
wherein $R^1$ is selected from the group consisting of 2-phenylacetyl, 2-phenoxyacetyl, 2-amino-2-phenylacetyl, 2-amino-2-[4-hydroxyphenyl]acetyl and 2-carboxy-2-phenylacetyl;

and Q is selected from the group consisting of hydrogen and methyl.

6. The method according to claim 5, wherein Q is hydrogen.

7. The method according to claim 6, wherein $R^1$ is 2-amino-2-phenylacetyl.

8. The method according to claim 6, wherein $R^1$ is 2-amino-2-[4-hydroxyphenyl]acetyl.

9. A pharmaceutical composition suitable for treating a bacterial infection in a mammalian subject, which comprises a pharmaceutically-acceptable carrier and an antibacterially effective amount of a compound of the formula

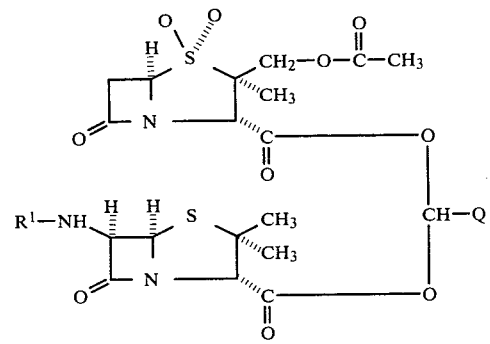

or a pharmaceutically-acceptable salt thereof,
wherein $R^1$ is selected from the group consisting of 2-phenylacetyl, 2-phenoxyacetyl, 2-amino-2-phenylacetyl, 2-amino-2-[4-hydroxyphenyl]acetyl and 2-carboxy-2-phenylacetyl;

and Q is selected from the group consisting of hydrogen and methyl.

* * * * *